United States Patent
Liu et al.

(10) Patent No.: US 12,187,770 B2
(45) Date of Patent: Jan. 7, 2025

(54) CYCLIC PEPTIDE FROM NOVEL BONE MORPHOGENETIC PROTEIN 2, PREPARATION METHOD THEREFOR AND APPLICATION THEREOF

(71) Applicant: Hangzhou Huibo Science and Technology Co., Ltd, Hangzhou (CN)

(72) Inventors: Yi Liu, Hangzhou (CN); Zhen Lin, Hangzhou (CN); Gang Wu, Hangzhou (CN)

(73) Assignee: HANGZHOU HUIBO SCIENCE AND TECHNOLOGY CO., LTD, Hangzhou (CN)

( * ) Notice: Subject to any disclaimer, the term of this patent is extended or adjusted under 35 U.S.C. 154(b) by 851 days.

(21) Appl. No.: 17/232,145

(22) Filed: Apr. 15, 2021

(65) Prior Publication Data
US 2021/0371485 A1    Dec. 2, 2021

Related U.S. Application Data

(63) Continuation-in-part of application No. PCT/CN2019/121809, filed on Nov. 29, 2019.

(30) Foreign Application Priority Data

Aug. 26, 2019   (CN) .......................... 201910790060.0

(51) Int. Cl.
*A61K 38/12* (2006.01)
*A61K 38/18* (2006.01)
(Continued)

(52) U.S. Cl.
CPC .............. *C07K 14/51* (2013.01); *A61K 38/12* (2013.01); *A61K 38/1875* (2013.01);
(Continued)

(58) Field of Classification Search
CPC ...... A61K 38/12; A61K 38/1709; C07K 7/50; C07K 14/51
See application file for complete search history.

(56) References Cited

U.S. PATENT DOCUMENTS

2015/0132354 A1* 5/2015 Roeder .............. A61K 38/1875
                                                          514/8.1
2019/0016770 A1   1/2019 Zouani

FOREIGN PATENT DOCUMENTS

| CN | 103665143 A | 3/2014 |
|---|---|---|
| CN | 108785657 | 11/2018 |
| KR | 100879704 B1 | 1/2009 |

OTHER PUBLICATIONS

Karoulias et al., Bone Reports, 2021, vol. 14:101092.*

(Continued)

*Primary Examiner* — Xiaozhen Xie
(74) *Attorney, Agent, or Firm* — MUNCY, GEISSLER, OLDS & LOWE, P.C.

(57) ABSTRACT

A cyclic peptide from a bone morphogenetic protein 2 (BrvIP2). The cyclic peptide from the novel BMP2 is selected from one of the following cyclic polypeptides: 1. a cyclic polypeptide having the sequence of CKIPKASSVP-TELSAISMLYLGPGGDWIVAC (SEQ ID NO:1); and 2. a cyclic polypeptide of which the sequence has an 80% homology with the sequence defined in item 1. A preparation method for the cyclic peptide from the novel Blv1P2, and an application thereof in the preparation of the composite material for promoting the repair of large-sized bone defects.

12 Claims, 8 Drawing Sheets
Specification includes a Sequence Listing.

(51) Int. Cl.
*A61P 19/08* (2006.01)
*C07K 1/107* (2006.01)
*C07K 1/16* (2006.01)
*C07K 14/51* (2006.01)
*A61K 38/00* (2006.01)

(52) U.S. Cl.
CPC ............ *A61P 19/08* (2018.01); *C07K 1/1075* (2013.01); *C07K 1/16* (2013.01); *A61K 38/00* (2013.01)

(56) References Cited

OTHER PUBLICATIONS

Saito et al., Biochim. Biophys. Acta, 2003, vol. 1651(1-2):60-67.*
Joo, S.H., Biomol. Ther., 2012, vol. 20(1):19-26.*
PCT/CN2019/121809 International Search Report dated Mar. 4, 2021 and English translation.

* cited by examiner

SEQUENCE LISTING

```
<160> NUMBER OF SEQ ID NOS: 4

<210> SEQ ID NO 1
<211> LENGTH: 31
<212> TYPE: PRT
<213> ORGANISM: unknown
<220> FEATURE:
<223> OTHER INFORMATION: modified cyclied polypeptide

<400> SEQUENCE: 1

Cys Lys Ile Pro Lys Ala Ser Ser Val Pro Thr Glu Leu Ser Ala Ile
1               5                   10                  15

Ser Met Leu Tyr Leu Gly Pro Gly Gly Asp Trp Ile Val Ala Cys
            20                  25                  30

<210> SEQ ID NO 2
<211> LENGTH: 22
<212> TYPE: PRT
<213> ORGANISM: unknown
<220> FEATURE:
<223> OTHER INFORMATION: cyclized polypeptide
```

```
<400> SEQUENCE: 2

Cys Lys Ile Pro Lys Ala Ser Ser Val Pro Thr Glu Leu Ser Ala Ile
1               5                   10                  15

Ser Met Leu Tyr Leu Cys
            20

<210> SEQ ID NO 3
<211> LENGTH: 20
<212> TYPE: PRT
<213> ORGANISM: unknown
<220> FEATURE:
<223> OTHER INFORMATION: linear peptide

<400> SEQUENCE: 3

Lys Ile Pro Lys Ala Ser Ser Val Pro Thr Glu Leu Ser Ala Ile Ser
1               5                   10                  15

Met Leu Tyr Leu
            20

<210> SEQ ID NO 4
<211> LENGTH: 29
<212> TYPE: PRT
<213> ORGANISM: unknown
<220> FEATURE:
<223> OTHER INFORMATION: modified linear peptide

<400> SEQUENCE: 4

Lys Ile Pro Lys Ala Ser Ser Val Pro Thr Glu Leu Ser Ala Ile Ser
1               5                   10                  15

Met Leu Tyr Leu Gly Pro Gly Gly Asp Trp Ile Val Ala
            20                  25
```

CYCLIC PEPTIDE FROM NOVEL BONE MORPHOGENETIC PROTEIN 2, PREPARATION METHOD THEREFOR AND APPLICATION THEREOF

CROSS-REFERENCE

The present application is a continuation-in-part of the International Application No. PCT/CN2019/121809 filed on Nov. 29, 2019, which claims priority to Chinese Invention Application No. 201910790060.0 filed on Aug. 26, 2019. All aforementioned patent applications are hereby incorporated by reference. All examples of the aforementioned patent applications are part of the present application.

SEQUENCE LISTING

The instant application contains a Sequence Listing which has been submitted electronically in ASCII format and is hereby incorporated by reference in its entirety. Said ASCII copy, created on Aug. 23, 2021, is named THIP0015_ST25.TXT and is 1,634 bytes in size. Applicant hereby states that the submission, filed in accordance with 37 CFR 1.821(e), herein does not include new matter.

TECHNICAL FIELD

The present invention relates to the field of biomedicine, in particular to a cyclized polypeptide from a novel bone morphogenetic protein 2, a preparation method therefor and an application thereof.

BACKGROUND

The introduction of this background is only a general introduction to help readers understand the present invention, and does not constitute any limitation to the present invention.

The repair of large-sized bone defects has always been one of the major issues that have not been overcome by medicine. Autologous bone transplantation has limited clinical application due to its long operation time and pain in the donor area and so on. Allogeneic bone transplantation, xenogeneic bone transplantation and most synthetic materials lack the potential to induce bone regeneration, so they cannot be used alone to repair large-sized bone tissue defects. Bone morphogenetic protein (BMP) has high efficiency in bone induction. BMP-2 in its family has been certified by the FDA and can be used for clinical treatments such as repairing bone defects and accelerating bone fusion. However, the production of BMP protein mainly relies on the method of genetic recombination, and its low yield, high clinical application cost, high immunogenicity and other side effects restrict its promotion. Therefore, bone repair materials based on small molecular polypeptides from BMP have become a research hotspot in the repair of large-sized bone defects.

Small molecular polypeptides can be chemically synthesized, with low cost and high yield. The polypeptide only contains the key functional peptides of the protein, and the structure is relatively simple, which can avoid the side effects caused by other domains in the macromolecular protein, so the polypeptide has low immunogenicity. In addition, polypeptides can be degraded into small amino acids in vivo, with no side effects and higher safety. However, straight-chain polypeptides with simple structures are easily degraded in vivo and are difficult to exert long-term effects.

For this reason, it is necessary to improve the existing traditional technology, hoping to obtain a better peptide structure and improve the repair effect of the peptide.

SUMMARY

The objective of the present invention is to overcome the above shortcomings and provide a cyclized polypeptide from a novel bone morphogenetic protein 2 a preparation method therefor and an application thereof.

The team of the present invention conducted a series of related studies on the effects of polypeptides from the specifically modified BMP2 by cyclization, and found that: 1) it could be seen from the experiment on osteogenic differentiation of mouse mesenchymal stem cells (BMSC) induced by BMP-2 protein, a linear peptide from BMP-2 and the cyclized polypeptide from BMP-2 of the present invention: the results of ALP staining showed that ALP induced by the cyclized polypeptide from BMP-2 of the present invention had obvious advantages over the linear peptide, and its efficacy was close to that of BMP-2 protein. Cell experiment in vitro confirmed that the cyclized polypeptide from BMP-2 could efficiently promote the adhesion, extension, migration, anti-inflammatory of mesenchymal stem cells, up-regulate the vascularization factors of stem cells, and activate mesenchymal stem cells-endothelial cells to form vascular-like tissues, with the ability to promote vascularization of 2.8 times higher than that of the positive control group; the control here was divided into three controls, a negative control: no addition; an experimental control: the linear peptide as a negative control for the effect of cyclization modification; a positive control, BMP2, a growth factor that had been identified as having osteoinductive properties, had been used in clinical practice, and was also a target replacement for cyclic peptide. 2) Animal experiment confirmed that the cyclized polypeptide from modified BMP2 support material could accelerate the healing of large-sized bone defects in the skull of rat faster than other groups.

Therefore, in one aspect, the present invention provides a cyclized polypeptide from bone morphogenetic protein 2 (BMP-2), which is selected from the following cyclized polypeptides, or a polypeptide of which the sequence has 80% homology with the sequence: CKIPKASSVPTELSA-ISMLYLGPGGDWIVAC (SEQ ID NO: 1). In some embodiments, the cyclic peptide sequence is a ring formed by linking sulfhydryl groups at the head and tail of an amino acid by oxidizing.

In some embodiments, the polypeptide may be artificially synthesized, or a polypeptide with multiple amino acid substitutions, deletions, and insertions.

The "cyclized polypeptide" described here can be a synthetic polypeptide with synthesis of all amino acid sequences, or a polypeptide and homologues thereof with individual or multiple amino acid substitutions, deletions, and insertion variants without affecting their essential functions by the alteration of some amino acids that is known to those skilled in the art.

In another aspect, the present invention provides a composite material for bone defect repair, wherein the material includes a cyclized polypeptide from bone morphogenetic protein 2, wherein the cyclized polypeptide has a sequence of CKIPKASSVPTELSAISMLYLGPGGDWIVAC (SEQ ID NO: 1) or a sequence having 80% homology with it.

In some embodiments, the composite material also includes one or a mixture of bioglass materials, degradable natural polymers, or some synthetic degradable polymer materials.

The cyclized polypeptide from specially modified BMP2 can significantly promote the repair of large-sized bone defects. It is combined with a variety of biological materials, so that different biological materials can achieve similar effects in promoting bone defect repair. The biological materials here are mainly used as carriers, in which the cyclized peptide from BMP-2 is encapsulated, mixed or treated to be released slowly in vivo, and exert biological activity continuously. Therefore, in some embodiments, the biocomposite materials involved may include a bioglass material such as dicalcium silicate, for example, a bioceramic such as hydroxyapatite, dicalcium phosphate, tricalcium phosphate, octacalcium phosphate, calcium sulfate and the like. These biological materials can also be degradable natural polymers, synthetic polymers or bioceramics, for example, specifically including one or more of natural materials such as chitosan, hyaluronate, sodium alginate, cellulose, starch, lignin, collagen, gelatin, carrageenan and so on, and derivatives thereof. It can also be one or more of synthetic polymer materials such as polylactic acid, polyglycolic acid, polycaprolactone, polyhydroxyalkanoate, polysiloxane, polyurethane and the like, and derivatives thereof. In some embodiments, it may also be a composite material composed of the above different materials, for example, it may include a bioglass material, a degradable natural polymer, or some synthetic degradable polymer material.

The cyclized polypeptide from specially modified BMP2 of the present invention can be combined with a variety of support carriers (with good biocompatibility and no impact on the activity of the polypeptide), and the type of carrier can be powder, granule, ointment. The specific material of the carrier can be hydrogel, membrane, sponge, fiber scaffold material, etc. Therefore, in some embodiments, the cyclized polypeptide from specially modified BMP2 has an amount of 0.01-10 µg per cubic centimeter of the carrier. Of course, these cyclized polypeptides from specially modified BMP2 can be mixed with the above biological material followed by treatment on the carrier, optionally, the cyclized polypeptides from specially modified BMP2 can be directly treated on the carrier.

The application of the cyclized polypeptide from specially modified BMP2 of the present invention can be implanted or covered on a bone defect site after being loaded by a support material.

The application dose of the cyclized polypeptide from specially modified BMP2 of the present invention is 0.01-10 µg/cm$^2$, but the dose and dose range for clinical application need to incorporate many factors, including the mode of administration, carrier, patient's physical condition and the size of the defect, etc.

The BMP2 protein is certified by FDA to be used to repair large-sized bone defects in clinic. The present invention modifies the effective amino acid sequence in the BMP2 protein, and the cyclized polypeptide from BMP2 has not been found to have acute toxicity in animals, and has good biological safety.

In some embodiments, the cyclized polypeptide of the present invention can be synthesized using solid-state synthesis. The solid phase method can effectively avoid side reactions such as dimerization, polymerization and the like during the cyclization process. As early as the 1960s, Fridkin et al. used a polymer carrier to synthesize a cyclized polypeptide. The C-terminal carboxyl group of the linear peptide forms an ester bond with resin and the linear peptide is hung on the resi, followed by neutralizing with triethylamine at room temperature for 12 h after removing N-terminal protective group, to obtain a cyclized polypeptide with a yield of 60%-80%, and the specific process is as follows: in recent years, the strategy of synthesizing a cyclized peptide by linking an amino acid side chain with resin has been widely used in the synthesis of a cyclized polypeptide. For linear polypeptides with aspartic acid or glutamic acid residues, carboxyl groups on the side chain of these two acidic amino acid residues can be selected as the C-terminals, which is condensed with PAC (alkoxybenzyl alcohol) or PAL (alkoxybenzylamine) or other types of resins, and the linear peptide is hung on the resin. Carboxyl groups on the main chain are protected with an allyl group. After gradually linking the peptide, N-terminal and C-terminal protective groups are removed, followed by adding a condensing agent to obtain a cyclized product attached to the resin. Finally, the cyclized peptide is cleaved from the resin with a mixture of trifluoroacetic acid: anisole sulfide: b-mercaptoethanol: anisole, while other side chain protecting groups are removed.

Therefore, in some embodiments, the material also includes a method for preparing a cyclized polypeptide from bone morphogenetic protein 2, including the steps of:

1. resin swelling: weighing 0.6-1 g of 2-Chlorotrityl Chloride Resin with a substitution degree of 0.2-0.4 mmol/g, placing the same into a reaction tube, and adding 15-20 ml of DCM under shaking for 30 min;
2. linking a first amino acid
   removing a solvent through a sand core suction filter, adding 2-to-4-fold excess of Fmoc-Cys(Trt)-OH amino acid in molar, and then adding 9-to-11-fold excess of DIEA in molar, followed by adding a small amount of DMF to dissolve under shaking for 1 h finally; and washing alternately with DMF and DCM for 6-8 times;
3. deprotection
   adding a 10-20 ml solution of 15-25% piperidine in DMF at 10-20 ml/g for 5 min, which is removed followed by adding a 10-20 ml solution of 15-25% piperidine in DMF at 10-20 ml/g for 15 min;
4. intermediate testing step
   the objective of the intermediate testing step is to determine whether the synthesized amino acid is successfully linked. Removing the piperidine solution by suction filtration to obtain the resin, from which 15-20 g of the resin is took and washed with ethanol for 2-4 times, adding 1-2 drops ninhydrin, KCN, and phenol solution separately, heating at 105° C.-110° C. for 5-10 min, and color change to dark blue indicates a positive reaction;
5. first washing
   washing twice with DMF at 5-15 ml/g, twice with methanol at 5-15 ml/g, and twice with DMF at 5-15 ml/g;
6. condensation
   adding 3-to-4-fold excess of a protected amino acid Fmoc-Leu-OH and 3-to-4-fold excess of HBTU, both dissolved in a small amount of DMF, into a reaction tube, followed by adding 9-to-11-fold excess of DIEA to react for 40 min;
7. second washing
   washing once with DMF at 5-15 ml/g, twice with methanol at 5-15 ml/g, twice with DMF at 5-15 ml/g;
8. repeating steps 2 to 7 to link amino acids in the sequence from right to left; for example, if the amino acid having a sequence of CKIPKASSVPTELSAISM- LYLGPGGDWIVAC (SEQ ID NO: 1) is needed to be synthesized, starting with amino acid C, followed by amino acid A, 9. testing washing 3-4 times with DMF at 5-15 ml/g, 2-4 times with DCM at 5-15 ml/g, twice with DMF at 5-15 ml/g, followed by draining for 10 min; and Ninhydrin test is negative;

10. third washing washing 3-4 times with methanol at 5-15 ml/g;

11. polypeptide cleavage from resin preparing a cleavage solution according to a ratio of 1 g resin to 10 ml cleavage solution containing 94.5% TFA, 2.5% water, 2.5% EDT, and 0.5% TIS;

placing the resin into a flask or a centrifuge tube based on a ratio of the resin and the cleavage solution at 5-15 ml/g under constant temperature shaking for 120 min;

12. blow drying and washing blow drying the cleavage solution with nitrogen, and then being subjected to chromatography with ether, followed by washing with ether for six times, and then drying by volatilization at room temperature; and obtaining a crude peptide sequence; and the obtained peptide has an amino acid sequence of CKIPKASSVP-TELSAISMLYLGPGGDWIVAC (SEQ ID NO: 1).

13. oxidative cyclization cyclizing 10 mg of the crude peptide sequence by adding 100-120 ml of 5-6% DMF solution to oxidize sulfhydryl groups. The so-called cyclization is to oxidize sulfhydryl groups at the head and tail of an amino acid C to form a cyclic peptide chain;

14. purifying the polypeptide by HPLC;

15. finally, lyophilizing the purified solution is to obtain the finished product.

Preferably, step 14 specifically includes:

1) placing 200 mg of the crude peptide into a container, dissolving with 2-5 ml of 50% acetonitrile in water, and being exposed to ultrasound for 2 min;

2) filtering the dissolved solution with a 0.45 μm filter membrane;

3) analysis: analyzing 3 μl of the crude product by analytical HPLC; with water and acetonitrile as a mobile phase, conducting a gradient elution for 30 min, and equilibrating HPLC firstly at an initial gradient of 95% water and 5% acetonitrile to a terminal ratio of 5% water and 95% acetonitrile for 5 min, and followed by injection;

4) preparation: making the dissolved sample ready for injection; equilibrating preparative HPLC for 10 min at an initial gradient of 95% water and 5% acetonitrile to a terminal gradient of 25% water and 75% acetonitrile for 40 min; collecting the sample from the detector;

5) identification: taking the collected sample for purification and MS identification.

Through MS identification, the result shows that the peptide chain of the present invention has been obtained and successfully cyclized. The details are shown in FIG. 1.

In some embodiments, the cyclic peptide of the present invention can also be synthesized by other methods, such as the active lipid method. In the active ester method, the activation of the carboxyl group and the cyclization reaction are carried out in two steps. The active ester generally can be used directly in the cyclization reaction without purification due to be relatively stable. Almost all active esters that can be used in coupling reactions can be used to synthesize cyclized peptides, mainly including p-nitrophenol ester, N-hydroxysuccinimide ester, pentafluorophenyl ester and 2,4,5-trichlorophenol ester. The C-terminal carboxyl group of linear peptide reacts with p-nitrophenol, N-hydroxysuccinimide, pentafluorophenol or 2,4,5-trichlorophenol, in the presence of DCC or other condensing agents, at low temperature, to easily obtain corresponding active esters. Such active ester with BOC or Z protection at the N-terminal is deprotected under acidic conditions to form the active ester hydrohalide in weakly basic dilute solution (a type of solvent with a large dielectric constant such as pyridine, DMF or dioxane) at pH 8-9 under heating (60-100° C.) or stirring at room temperature for several hours to several days, to obtain the cyclized peptide finally.

In other embodiments, the azide method is another classic method in peptide synthesis, having the advantage of rarely racemization, which is first used in the synthesis of linear peptides and is now often used in the synthesis of cyclized peptides. Specifically, the methyl ester, ethyl ester, benzyl ester, substituted benzyl ester, or other more active esters of linear peptides are subjected to form hydrazide by hydrazinolysis, followed by dissolving in acetic acid or a hydrochloric acid-acetic acid mixed solution, and then adding 1 M of sodium nitrite solution at about −5° C. to generate nitrous acid that reacts with hydrazide to form azides. The linear peptide azide with N-terminal free is stirred at 4° C. for one day and then warmed to room temperature to obtain cyclized peptides.

In some methods, enzymatic methods can also be used to synthesize polypeptides. The use of protease in buffer to synthesize cyclized peptides is also one of the methods under development. Jackson et al. reported that several cyclized peptides containing 12-25 amino acid residues connected head to tail were synthesized by enzymatic cyclization with derivatives of linear peptide esters as substrates, in which the enzyme Subtiligase used for cyclization was the product of subtilisin mutation, and the catalytic reaction system was a buffer solution at pH=8. They were detected by HPLC with a yield between 30% and 80%. The efficiency of cyclization was related to the sequence and length of the peptide. The minimum length of the linear peptide required to synthesize cyclized peptides by Subtiligase was 12 amino acid residues, below which a hydrolysate or linear peptide dimerization product would be obtained. It might be that the head-to-tail spatial conformation formed by peptide substrates of less than 12 residues could not match the active center of the enzyme.

The beneficial effects of the present invention are:

1) a cyclized polypeptide from modified BMP2 used in the present invention has high efficiency in inducing osteogenesis, and can effectively promote the repair of large-sized bone defects. 2) A cyclized polypeptide from specially modified BMP2 used in the present invention is a human-derived polypeptide, which has good biocompatibility and no side effects such as immune rejection. 3) A cyclized polypeptide from specially modified BMP2 used in the present invention can be loaded on a variety of biological materials and has a wide range of application prospects.

DETAILED DESCRIPTION OF THE EMBODIMENTS

Figure 1:
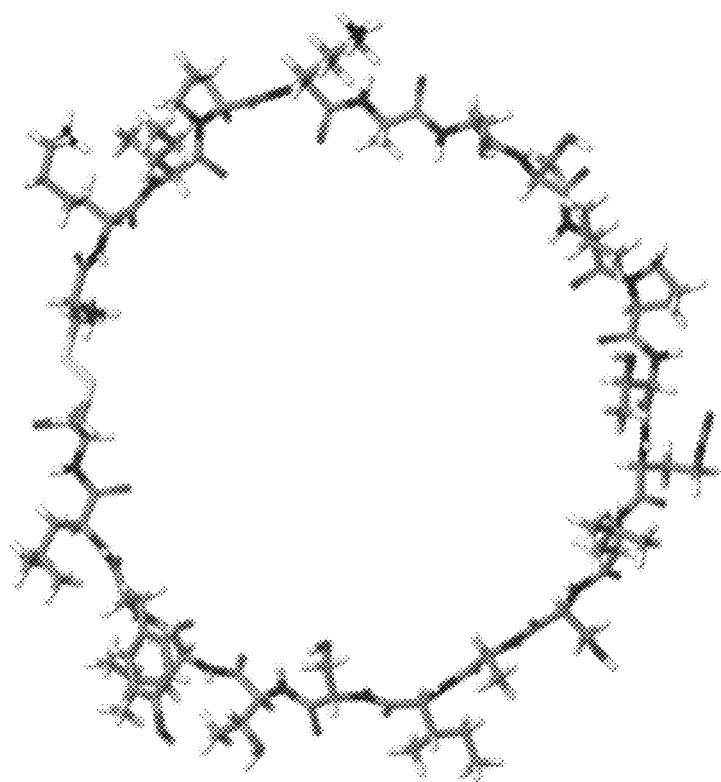
FIG. 1 is a schematic diagram of the structure of a cyclized polypeptide from BMP2 in a specific embodiment.

The present invention will be further described below in conjunction with embodiments. The description of the following embodiments is only used to help understand the specific implementation of the present invention. It should be pointed out that for those of ordinary skill in the art, several improvements and modifications can be made to the present invention without departing from the essence of the principles of the present invention, and these improvements and modifications also fall within the protection scope of the claims of the present invention, and the protection scope of the present invention is subject to the claims.

Synthesis Example 1

CKIPKASSVPTELSAISMLYLGPGGDWIVAC
(SEQ ID NO:1) Solid-Phase Polypeptide Synthesis

The specific steps were as follows:
1. Resin swelling
0.8 g of 2-Chlorotrityl Chloride Resin with a substitution degree of 0.35 mmol/g was weighed and placed into a reaction tube with addition of DCM (concentration: 15 ml/g) under shaking for 30 min.
2. Linking a first amino acid
Solvent DCM was removed through a sand core suction filter, with addition of 3-fold excess of Fmoc-Cys(Trt)-OH amino acid in molar, and then 8-fold excess of DIEA (N,N-Diisopropylethylamine) in molar were added, followed by adding a small amount of DMF to dissolve under shaking for 1 h finally. They were washed alternately with DMF and DCM for 6 times
3. Deprotection
a 15 ml solution of 20% piperidine in DMF (15 ml/g) was added for 5 min, which was removed followed by adding a 15 ml solution of 20% piperidine in DMF (15 ml/g) for 15 min.
4. testing
The piperidine solution was removed by suction filtration to obtain the resin, from which dozens of resins were took and washed with ethanol for 3 times, with addition of one drops of ninhydrin, KCN, and phenol solutions separately, followed by heating at 105° C.-110° C. for 5 min, and color change to dark blue indicated a positive reaction.
5. Washing
Washing twice with DMF (10 ml/g), twice with methanol (10 ml/g), and twice with DMF (10 ml/g).
6. Condensation
Three-fold excess of a protected amino acid (Fmoc-Leu-OH) and three-fold excess of HBTU, both dissolved in a small amount of DMF, were added into a reaction tube, followed by adding ten-fold excess of DIEA to react for 40 min.
7. Washing
Washing once with DMF (10 ml/g), twice with methanol (10 ml/g), and twice with DMF (10 ml/g);
8. Steps 2 to 7 were repeated to link amino acids in the sequence from right to left.
9. testing
Washing twice with DMF (10 ml/g), twice with DCM (10 ml/g), twice with DMF (10 ml/g), followed by draining for 10 min. Ninhydrin test was negative.
10. Washing
Washing 3 times with methanol (10 ml/g).
11. Polypeptide cleavage from resin
Preparing a cleavage solution (10/g): 94.5% TFA, 2.5% water, 2.5% EDT, and 1% TIS
Resin was placed into a flask or a centrifuge tube based on a ratio of the resin and the cleavage solution at 10 ml/g under constant temperature shaking for 120 min.
12. Blow drying and washing
The cleavage solution was blow dried with nitrogen as much as possible, and then was subjected to chromatography with ether, followed by washing with ether for six times, and then drying by volatilization at room temperature. The crude peptide sequence was obtained.
13. Oxidative cyclization
10 mg of the crude produce were cyclized by adding 100 ml of 5% DMF solution to oxidize sulfhydryl groups.
14. Purifying the polypeptide by HPLC, with the specific steps of:
1) 200 mg of crude peptides were placed into a container. They were dissolved with 2-5 ml of 50% acetonitrile in water. They could be sonicated slightly for 2 min.
2) The dissolved solution was filtered with a 0.45 μm filter membrane.
3) Analysis: 3 μl of the crude product was analyzed by analytical HPLC. The mobile phase was water and acetonitrile conducting a gradient elution for 30 min, and equilibrating HPLC firstly at an initial gradient of 95% water and 5% acetonitrile to a terminal ratio of 5% water and 95% acetonitrile for 5 min, and followed by injection.
4) Preparation: the dissolved sample was made ready for injection. Preparative HPLC was equilibrated for 10 min at an initial gradient of 95% water and 5% acetonitrile to a terminal gradient of 25% water and 75% acetonitrile for 40 min. The sample from the detector was collected.
5) identification: taking the collected sample for purification and MS identification.
15. Finally, the purified solution was lyophilized to obtain the finished product.
16. The powdered peptide was in a sealed package and stored at −20° C.

Synthesis Example 2

CKIPKASSVPTELSAISMLYLGPGGDWIVAC
(SEQ ID NO:1) Solid-Phase Polypeptide Synthesis

The specific steps were as follows:
1. Resin swelling
0.9 g of 2-Chlorotrityl Chloride Resin with a substitution degree of 0.3 mmol/g was weighed and placed into a reaction tube with addition of DCM (concentration: 18 ml/g) under shaking for 30 min.

2. Linking a first amino acid

Solvent was removed through a sand core suction filter, with addition of 3-fold excess of Fmoc-Cys(Trt)-OH amino acid in molar, and then 10-fold excess of DIEA in molar were added, followed by adding a small amount of DMF to dissolve under shaking for 1 h finally. They were washed alternately with DMF and DCM for 6 times 3. Deprotection a solution 18 ml of 20% piperidine in DMF (15 ml/g) was added for 5 min, which was removed followed by adding a 15 ml solution of 20% piperidine in DMF (15 ml/g) for 15 min.

4. testing

The piperidine solution was removed by suction filtration to obtain the resin, from which 15 g of resins were took and washed with ethanol for 3 times, with addition of one drops each of ninhydrin, KCN, and phenol solutions, followed by heating at 105° C.-110° C. for 5 min, and color change to dark blue indicated a positive reaction.

5. Washing

Washing twice with DMF (10 ml/g), twice with methanol (10 ml/g), and twice with DMF (10 ml/g).

6. Condensation

Three-fold excess of a protected amino acid (Fmoc-Leu-OH) and three-fold excess of HBTU, both dissolved in a small amount of DMF, were added into a reaction tube, followed by adding ten-fold excess of DIEA. The reaction was lasted for 40 min.

7. Washing

Washing once with DMF (10 ml/g), twice with methanol (10 ml/g), and twice with DMF (10 ml/g).

8. Steps 2 to 7 were repeated to link amino acids in the sequence from right to left.

9. testing

Washing twice with DMF (10 ml/g), twice with DCM (10 ml/g), twice with DMF (10 ml/g), followed by draining for 10 min. Ninhydrin test was negative.

10. Washing

Washing 3 times with methanol (10 ml/g).

11. Polypeptide cleavage from resin

Preparing a cleavage solution (10 ml): 94.5% TFA, 2.5% water, 2.5% EDT, and 1% TIS Resin was placed into a flask or a centrifuge tube based on a ratio of the resin and the cleavage solution at 1 g:10 ml under constant temperature shaking for 120 min.

12. Blow drying and washing

The cleavage solution was blow dried with nitrogen as much as possible, and then was subjected to chromatography with ether, followed by washing with ether for seven times, and then drying by volatilization at room temperature. The crude peptide sequence was obtained.

13. oxidative cyclization 10 mg of the crude produce were cyclized by adding 100 ml of 5% DMF solution to oxidize sulfhydryl groups.

14. Purifying of the polypeptide by HPLC

The specific steps were as follows:

1, 200 mg of crude peptides were placed into a container. They were dissolved with 4 ml of 50% acetonitrile in water. They could be sonicated slightly for 2 min.

2, The dissolved solution was filtered with a 0.45 μm filter membrane.

3, Analysis: 3 μl of the crude product was analyzed by analytical HPLC. The mobile phase was water and acetonitrile conducting a gradient elution for 30 min, and equilibrating HPLC firstly at an initial gradient of 95% water and 5% acetonitrile to a terminal ratio of 5% water and 95% acetonitrile for 5 min, and followed by injection.

4, Preparation: the dissolved sample was made ready for injection. Preparative HPLC was equilibrated for 10 min at an initial gradient of 95% water and 5% acetonitrile to a terminal gradient of 25% water and 75% acetonitrile for 40 min. The sample from the detector was collected.

5, Identification: the collected sample was took for purification and MS identification.

15. Finally, the purified solution was lyophilized to obtain the finished product.

16. The powdered peptide was in a sealed package and stored at −20° C.

Figure 2:
FIG. 2 is a schematic diagram of the structure of BMP type I receptor in a specific embodiment.
Figure 3:
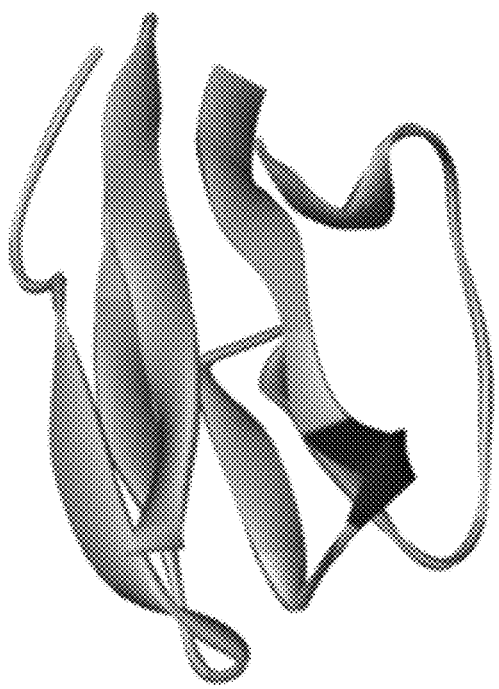
FIG. 3 is a structural diagram of VEGF type 2 receptor in a specific embodiment.
Figure 4:
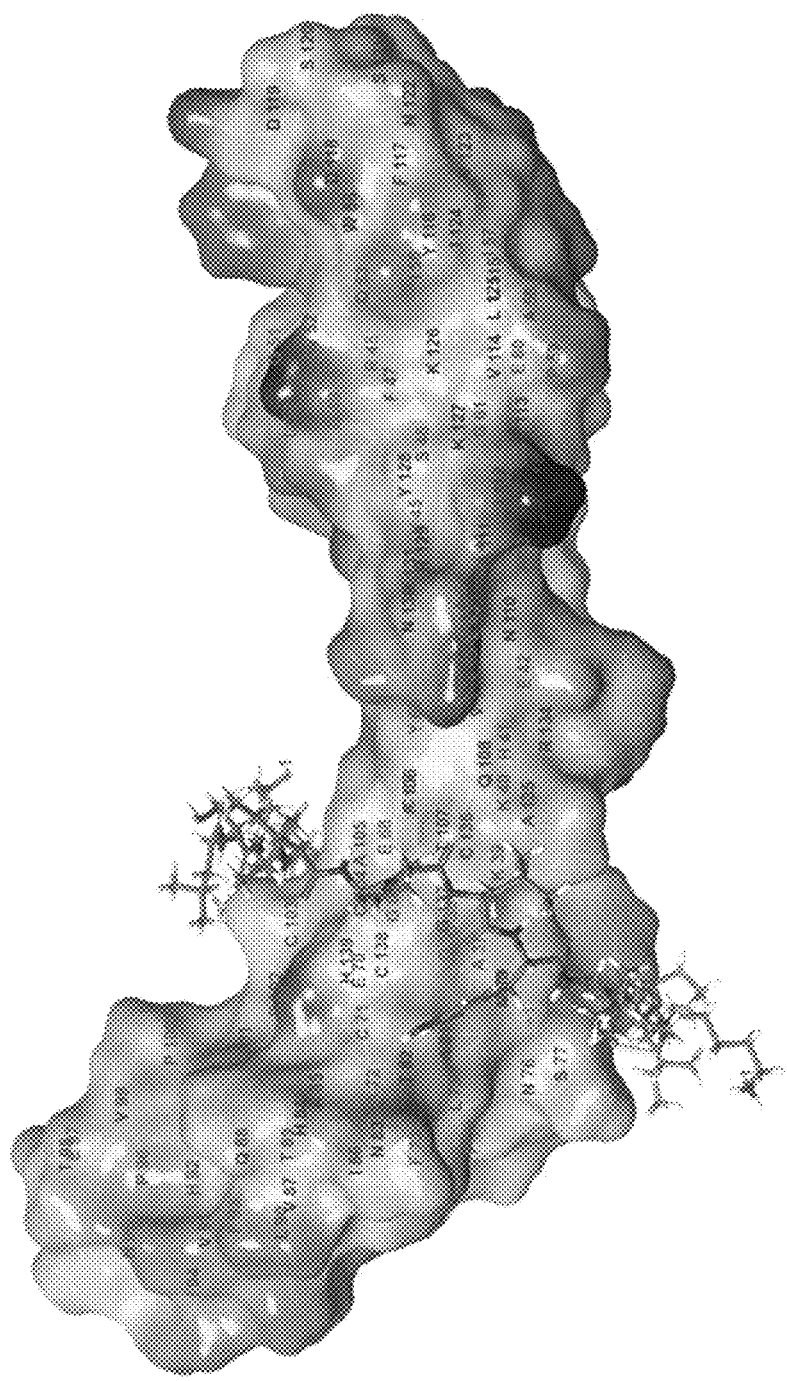
FIG. 4 is a schematic diagram of the optimal docking structure between a cyclic polypeptide from BMP2 of the present invention and BMP type I receptor molecule.
Figure 5:
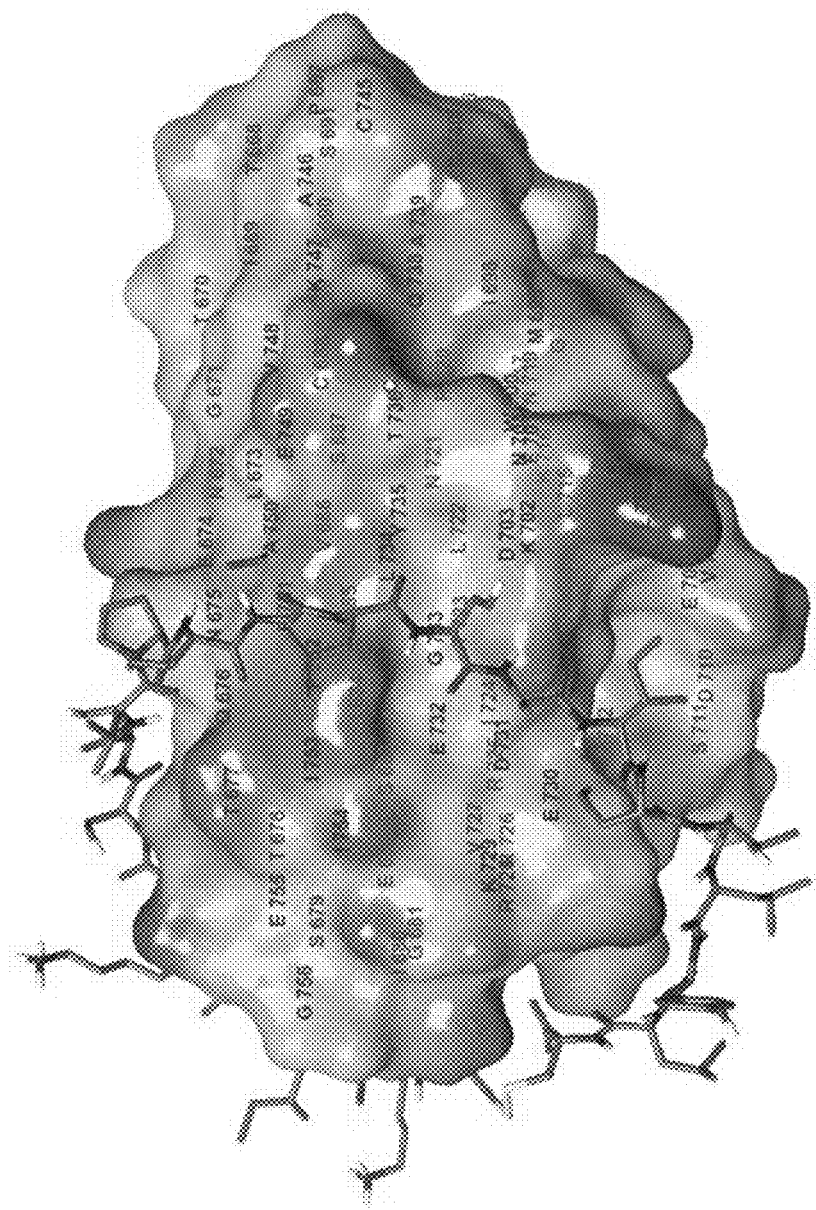
FIG. 5 is a schematic diagram of the optimal docking between a cyclized polypeptide from BMP2 and VEGF type 2 receptor molecule.

FIGS. 1 to 5 showed schematic diagrams of docking between the cyclized polypeptide from modified BMP2 with BMP type I and VEGF type 2 receptors. The cyclized polypeptide from BMP2 had high affinity for BMP type I receptor and VEGF type 2 receptor simultaneously, which enabled the cyclized polypeptide from BMP2 to rapidly induce receptor complex formation and mediate its intracellular signaling pathway. Wherein, FIG. 1: a structure diagram of a cyclized polypeptide form BMP2; FIG. 2: BMP I type receptor; FIG. 3: VEGF type 2 receptor; FIG. 4: surface interaction in an optimal structural diagram of docking between a cyclized polypeptide from BMP2 and BMP type I receptor molecule, wherein blue represented the positive surface area, red represented the negative surface area, and green represented the hydrophobic surface area; FIG. 5: a optimal structural diagram of docking between a cyclized polypeptide from BMP2 and VEGF type 2 receptor molecule.

Example 3

Promoting the Repair of Cranial Defects in Rats by Dripping a Cyclized Polypeptide from BMP2 Alone Study The specific operation was as follows: SD rats were anesthetized with 3% pentobarbital sodium by intraperitoneal injection, prone on the operating table, fixed limbs, shaved the parietal bones, and covered with 1% iodine disinfection drape. The skin fascia periosteum was cut in layers, and the skull parietal bone was exposed, then the skull parietal bone was cut with a 1 cm trephine using an implanter at 600 rpm, until it turned into a blue-purple ring near the skull. The bone fragment from one end was pried with a stripper, and 8 mm circular bone fragment was removed by a vascular forcep.

The cyclized polypeptide from modified BMP2 of the present invention (CKIPKASSVPTELSAISMLYLGPGGDWIVAC) (SEQ ID NO:1) (50 ng/mL), and the modified linear polypeptide of the present invention (KIPKASSVPTELSAISMLYLGPGGDWIVA) (SEQ ID NO:4) (50 ng/mL), a simple cyclized peptide at a concentration of 50 ng/mL (CKIPKASSVPTELSAISMLYLC) (SEQ ID NO: 2), 50 ng/mL of a simple linear polypeptide (KIPKASSVPTELSAISMLYL) (SEQ ID NO: 3), BMP2 protein (50 ng/mL) and equivalent saline (control) were respectively dripped on the medical collagen membrane, then the membrane was implanted into the skull defect site, and the periosteum and skin were sutured in layers and disinfected with iodine. Within 3 days after surgery, rats were injected daily with gentamicin for preventation infection and carprofen for analgesia, and they were fed normally in separate cages. Four weeks later, samples were taken for Micro-CT scanning, and the software was used to analyze the indicators of new bone formation.

Figure 8A:
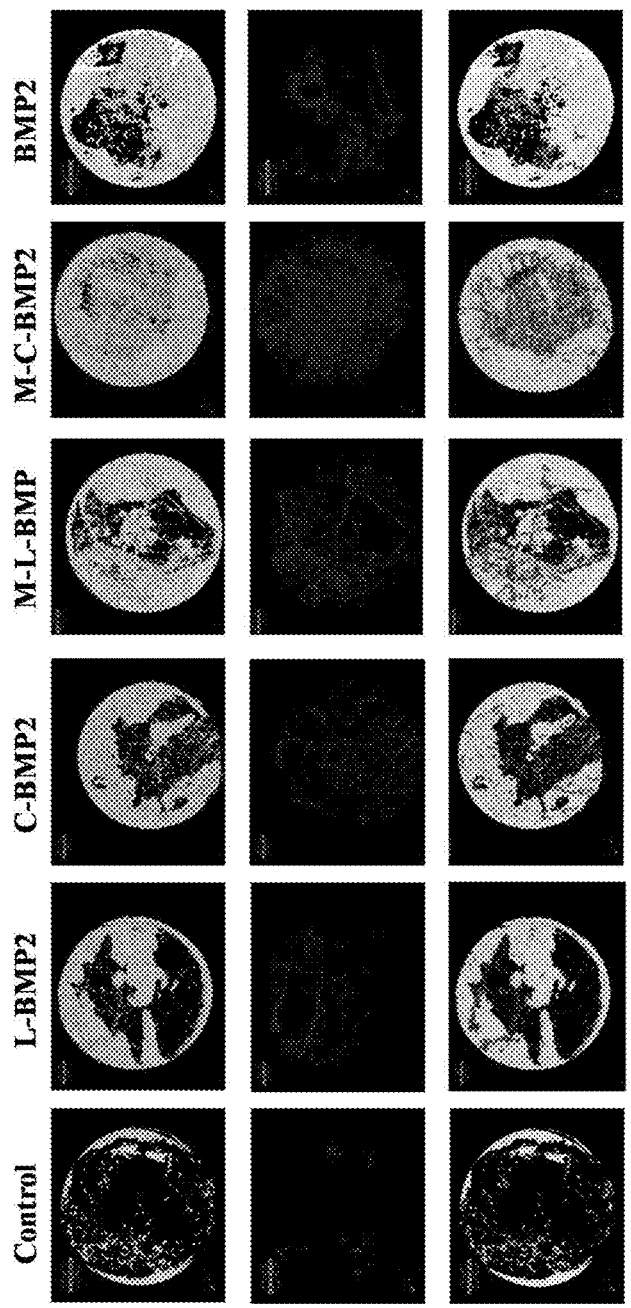
FIG. 8A is a diagram showing the results of three-dimensional reconstruction of new bone and new blood vessels by Micro-CT scan.
Figure 8C:
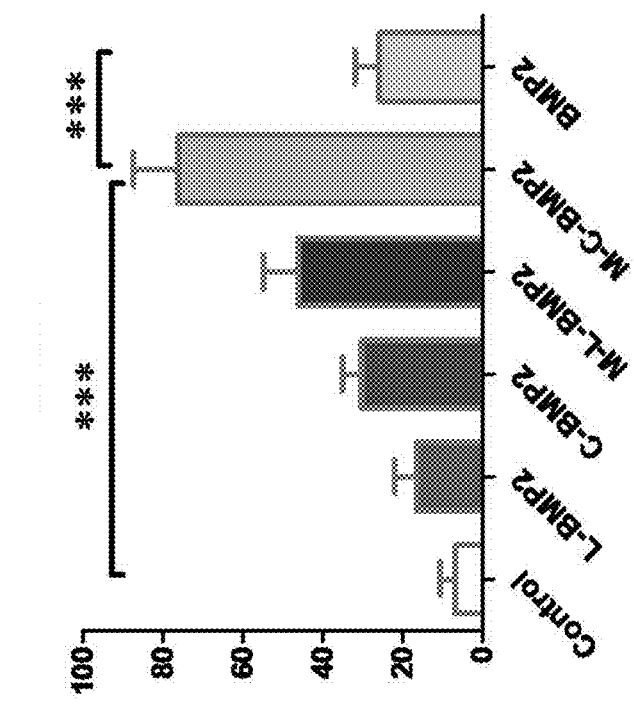
FIGS. 8B-8C are data statistics charts related to FIG. 8A.
Figure 8B:
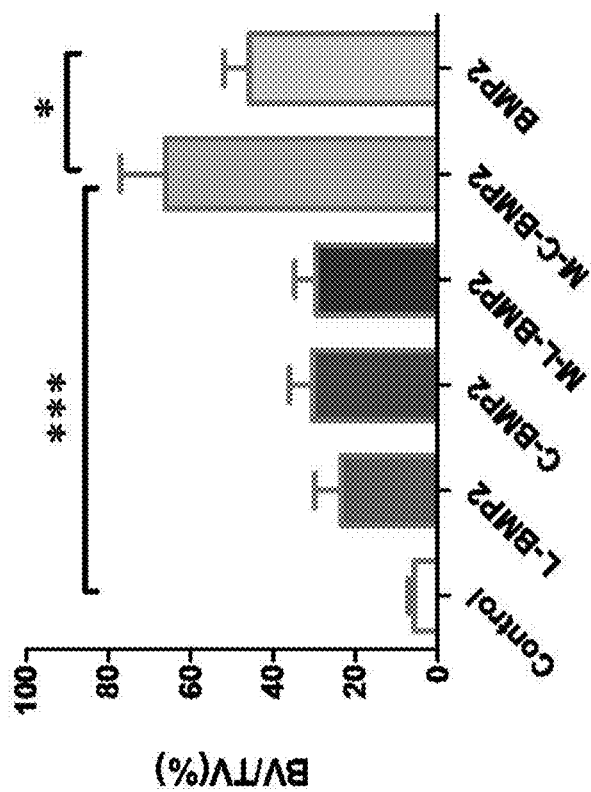

As shown in FIGS. 8A-8C, there was a round standard bone defect with a diameter of 8 mm in Wistar rat skull. The equivalent polypeptide or protein was loaded on the medical collagen membrane and then implanted into the bone defect area. After 4 weeks, Microfil perfusion and Micro-CT scan were performed to calculate the results of new bone and vascular reconstruction. (L-BMP2: a linear peptide (SEQ ID NO: 3); C-BMP2: a cyclized polypeptide (SEQ ID NO: 2); M-L-BMP2: a modified linear peptide (SEQ ID NO: 4); M-C-BMP2: a modified cyclized polypeptide (SEQ ID NO: 1); the last group: BMP2 protein, set as a control group).

The data statistics chart on the left showed that the volume ratio of new bone in the modified circlized peptide group was significantly higher than that of other groups with statistically difference (FIG. 8B). From the data in FIG. 8B, it could be seen that, overall, the effect of the cyclized polypeptide was greater than that of the linear peptide, but the modified cyclized polypeptide of the present invention had the best effect, which was significantly different from other treatment, and it had better effect than the protein. The figure on the right showed that the area of new blood vessels in the modified cyclized polypeptide group was higher than that of other groups (FIG. 8C), which was significantly different from the BMP2 protein group.

Example 4

The Collagen Sponge Loaded with a Cyclized Polypeptide from BMP2 is Used to Promote the Repair of the Limit Bone Defect of the Rat Skull The cyclized polypeptide from unmodified BMP2, modified linear polypeptide, simple cyclized polypeptide, simple linear polypeptide, BMP2 protein and equivalent saline were dissolved in normal saline, respectively, and they were evenly drop on the collagen sponge (the diameter of 0.5 cm, the thickness of 1 mm, the volume of 50 μl, each peptide or protein had equivalent concentration). After lyophilization, they were sealed and stored at low temperature. The pre-prepared sponge was implanted into the skull defect. After 4 weeks of sampling, MicroCT showed that compared with the blank control group, equivalent cyclized polypeptide from BMP2 had a significant effect on promoting new bone formation with the amount of new bone nearly twice that of the blank group.

Example 5

Effect of a Linear Peptide and a Cyclized Polypeptide on Human Osteoblast Cell Line (hFOB1.19), respectively.

5.1 Osteogenesis-Related Protein Expression Detection
  a) hFOB1.19, BMSC cell ALP activity detection and staining: ALP activity was detected using LabAssay™ ALP colorimetric assay kit, and the total protein concentration was measured by BCA method for calibration. After 7 days of culture, the cells were fixed for alkaline phosphatase staining. The specific operation of activity detection was as follows:
    ① The medium in the well plate was discarded and the plate was washed three times with PBS.
    ② Cells were lysed by adding cell lysate, and were crushed by ultrasound to promote the release of cell protein.
    ③ The supernatant was pipetted after centrifugation for 15 min (4° C., 15000 rpm) with addition of ALP detection buffer, followed by incubating at 37° C. for 30 min.
    ④ Stop solution was added to stop the reaction, and the absorbance at 405 nm wavelength was measured. ALP vitality was calculated.
    ⑤ Total cell protein was quantified by BCA method and the ALP activity was corrected.
  The specific method of ALP staining was as follows:
    ① The original medium was discarded and washed 3 times with PBS.
    ② Cells were fixed with 4% paraformaldehyde for 20 min;
    ③ Washing 3-5 times with PBS, 3-5 min each time;
    ④ BCIP/NBT staining working solution was formulated according to instructions of the kit;
    ⑤ After the last washing, the washing solution was removed, followed by adding 500 ul BCIP/NBT dyeing working solution to each well to ensure that the sample could be fully covered;
    ⑥ After incubation at 37° C. in an incubator in the dark for 30 min, the BCIP/NBT staining working solution was removed, and washed 1-2 times with PBS to stop the color reaction.
  b) Cell secretion type I collagen staining detection: after culture for 14 days, cells were washed 2 times with PBS after removal of medium, followed by washing 2 times with deionized water after fixation, and then stained with the kit, and dried and took pictures after washing.

5.2 Outer Matrix Mineralization Detection
  a) Extracellular matrix Alizarin Red staining: after cell inoculation and culture, cells were washed 2 times with PBS, followed by washing 2 times with deionized water after fixation, and stained with Alizarin red solution, then washed with deionized water until calcium nodules becoming red to remove excess dye solution, followed by drying and observation.
  b) Correlation area analysis: photographs and image data analysis: each group of cell culture wells was took picture by NIS-Elements F2.20 (Nikon Eclipse 80i), and the area of red-stained calcified nodules in each culture well was measured by Image-Pro Plus 6.0 software.

Figure 6:
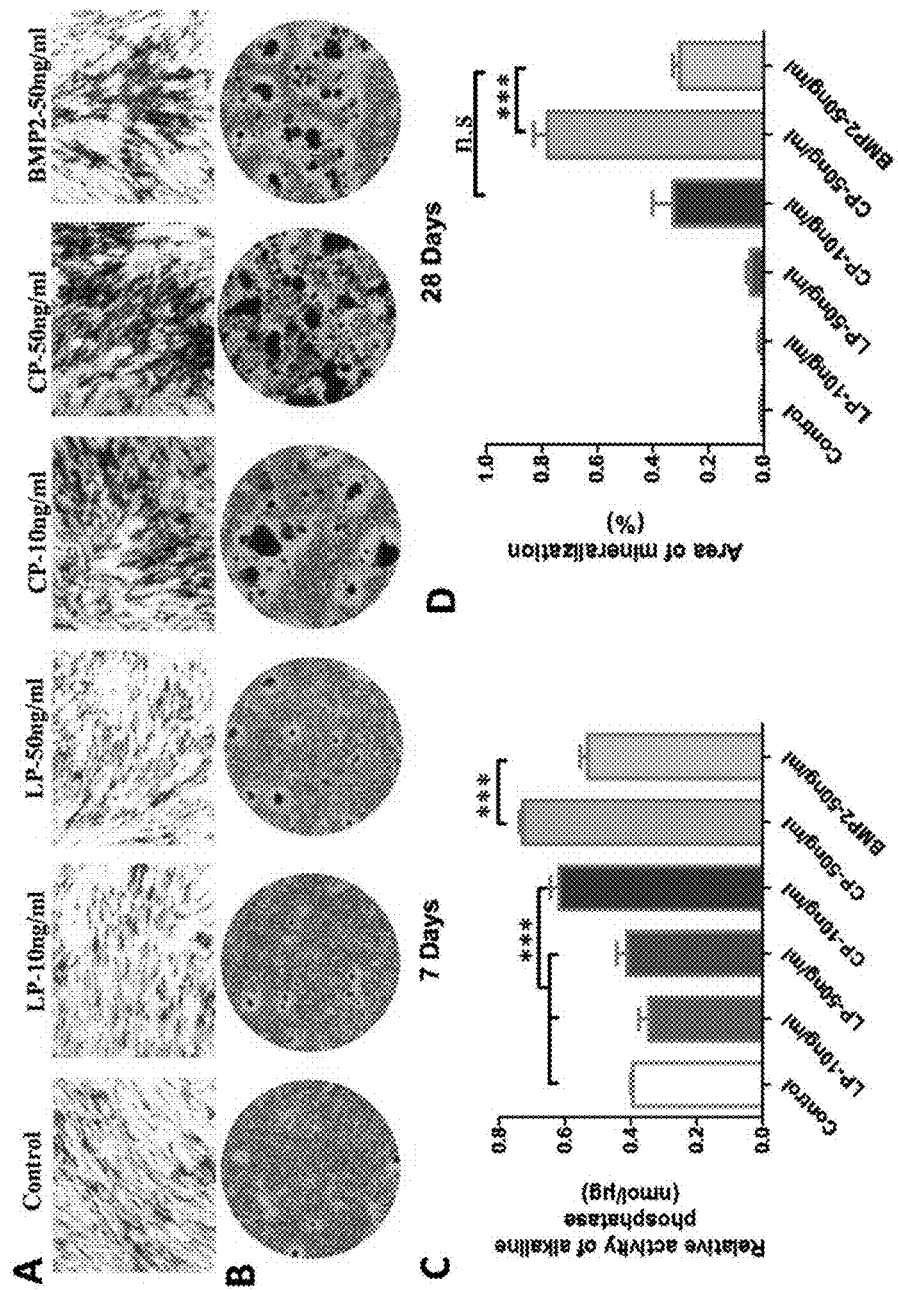
FIG. 6 is a diagram showing the results of detecting bone formation related indicators.

The above was only the general treatment process for the cells, and the specific concentration was shown in FIG. 6.

Result:

As shown in FIG. 6, the linear peptide and cyclized polypeptide of the present invention were used to detect osteogenic indicators by acting on the human osteoblast cell line (hFOB1.19): in FIG. 6, (A) indicates that ALP staining after culture for 7 days showed that the osteogenic effect of the cyclized polypeptide was significantly better than that of the linear peptide, and the effect of 50 ng/ml cyclized peptide was better than that of protein BMP2. (B) indicated that after induction culture in the mineralization medium for 28 days, Alizarin Red staining showed that the area of mineralized nodules induced by equivalent concentration of cyclized polypeptide was significantly higher than that of equivalent protein BMP2. (C) indicated that the quantitative detection of ALP after culture for 7 days revealed that the amount of ALP induced by 50 ng/ml cyclized peptide was significantly higher than that of protein BMP2. (D) indicated that the 28-day Alizarin Red quantitative analysis showed that the amount of mineralized nodules induced by 50 ng/ml cyclic peptide was 2.6 times higher than that induced by equivalent protein BMP2. (LP: a modified linear peptide of the present invention; CP: a modified cyclized polypeptide of the present invention; last group: BMP2 protein.*p<0.05; p<0.01; *p<0.001 had a significant difference; n.s.: no difference).

Example 6

Figure 7:
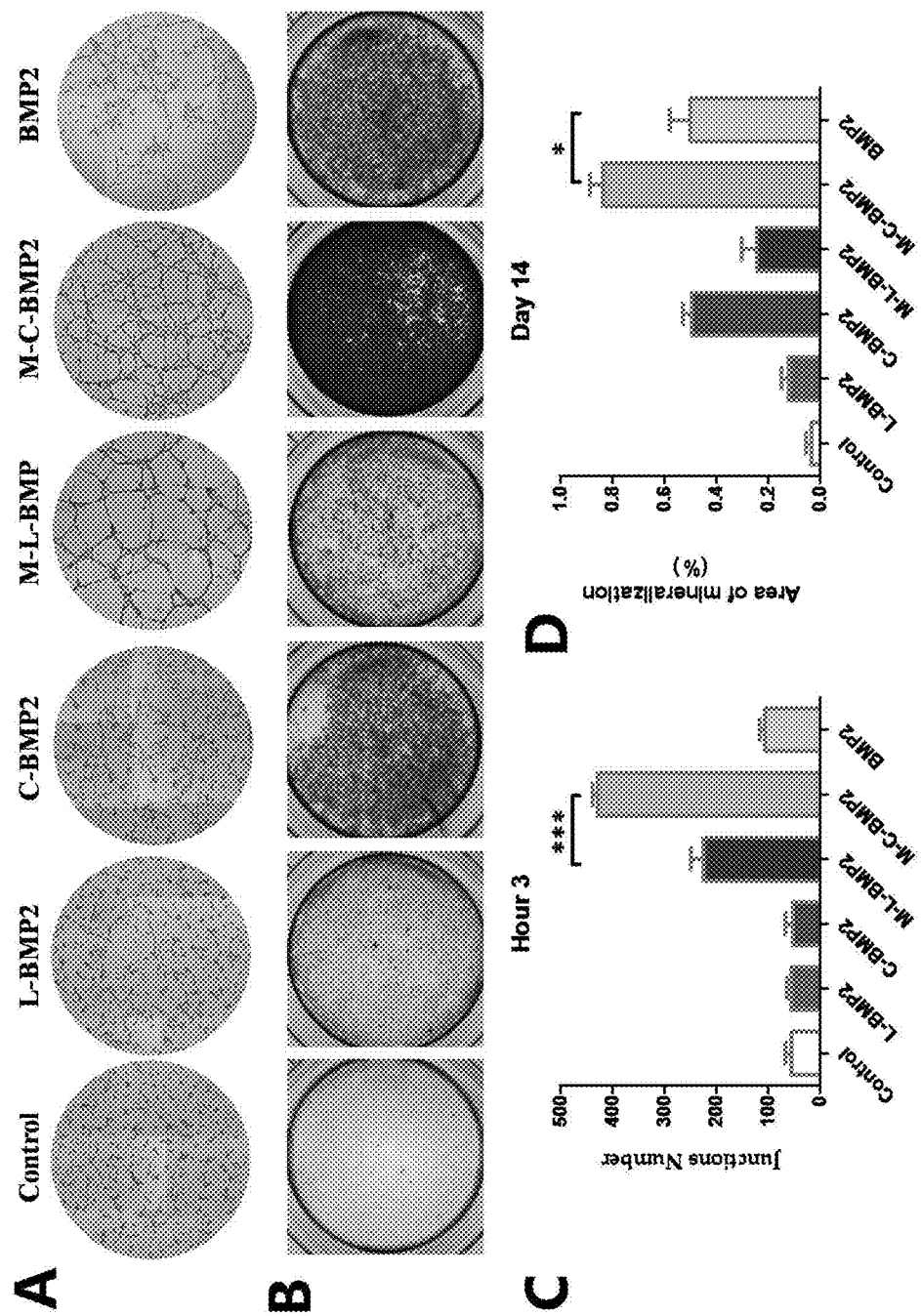
FIG. 7 is a diagram showing the results of observing the connection of cells in a tubular shape.

Four Peptides and Proteins Act on HUVEC and BMSC, Respectively
The Specific Operation Steps were as Follows: Osteogenesis Related Index Test was as FOB Cell Tube Formation Test
  a) On the first day, the matrigel was placed in a refrigerator at 4° C. overnight.
  b) On the next day, the matrigel was centrifuged for a few minutes after freezing and thawing.
  c) Operation was carried out on ice. Matrigel was mixed with a pre-cooled pipette tip in the pre-cooled EP tube, and aliquoted into 500 µl.
  d) The 96-well plate was pre-cooled in advance, with addition of 50 µl of matrigel to each well with avoiding air bubbles. It was placed at 37° C. in an incubator for 45 min.
  e) When the HUVEC cells were 70-80% confluence, they were digested and resuspended in DMEM containing 10% FBS. 50 µl of the resuspension solution was added to each well at a concentration of 3×10000 cells per well, with three duplicate wells.
  f) After incubation at 37° C. in an incubator, blood vessel formation could be seen after four hours.
Result:
As shown in FIG. 7, the four peptides and proteins acted on HUVEC and BMSC respectively to detect angiogenesis and osteogenic indicators: (A) Cell tubular morphology observation after 3 hours showed that the modified cyclized polypeptide had the best effect. (B) The result of extracellular matrix mineralization after 14 days showed that the new mineralized nodules of modified cyclized polypeptide were significantly higher than those of other groups. (C) The statistical analysis of tube forming junction points showed that the number of nodes induced by the modified cyclized polypeptide was four times that of the BMP2 protein group. (D) The statistical analysis of the area of mineralized nodules showed that the modified cyclized polypeptide had a more obvious promotion effect on the formation of mineralized nodules than BMP2 protein. (L-BMP2: a linear peptide (SEQ ID NO: 3); C-BMP2: a cyclized polypeptide (SEQ ID NO: 2); M-L-BMP2: a modified linear peptide (SEQ ID NO: 4); M-C-BMP2: a modified cyclized polypeptide (SEQ ID NO: 1); the last group: BMP2 protein. Each treatment had equivalent concentration. p<0.05; p<0.01; *p<0.001 had a significant difference; n. s: no difference).

In the absence of any elements or limitations specifically disclosed herein, the invention shown and described herein can be realized. The terms and expressions which have been employed are used as terms of description and not of limitation, and there is no intention in the use of such terms and expressions of excluding any equivalents of the features shown and described or portions thereof, and it is recognized that various modifications are possible within the scope of the invention. It is therefore to be understood that, although the present invention has been particularly disclosed by various embodiments and optional features, modifications and variations of the concepts herein described may be resorted to by a person skilled in the art, and that such modifications and variations are considered to fall within the scope of the present invention as defined by the appended claims.

The contents of the articles, patents, patent applications, and all other documents and electronically available information described or described herein are hereby incorporated by reference in their entirety to the same extent as if each individual publication was specifically and individually indicated to be incorporated by reference. Applicants hereby incorporate into this application any and all materials and information retained from any such article, patent, patent application or other document.

The invention claimed is:

1. A cyclic peptide from a modified bone morphogenetic protein 2, having the sequence of CKIPKASSVPTELSA-ISMLYLGPGGDWIVAC (SEQ ID NO: 1).

2. The cyclic peptide according to claim 1, wherein the cyclic peptide is synthesized by a method comprising the steps of:
1) resin swelling: weighing 0.6-1 g of 2-Chlorotrityl Chloride Resin with a substitution degree of 0.2-0.4 mmol/g, placing the same into a reaction tube, and adding 15-20 ml of DCM under shaking for 30 min;
2) linking a first amino acid: removing a solvent through a sand core suction filter, adding 2-to-4-fold excess of Fmoc-Cys (Trt)-OH amino acid in molar, and then adding 9-to-11-fold excess of DIEA in molar, followed by adding a small amount of DMF to dissolve under shaking for 1 h finally; and washing alternately with DMF and DCM for 6-8 times;
3) deprotection: adding a 10-20 ml solution of 15-25% piperidine in DMF at 10-20 ml/g for 5 min, which is removed followed by adding a 10-20 ml solution of 15-25% piperidine in DMF at 10-20 ml/g for 15 min;
4) testing: removing the piperidine solution by suction filtration to obtain the resin, from which 15-20 g of the resin is took and washed with ethanol for 2-4 times, adding 1-2 drops of ninhydrin, KCN and phenol solutions separately, heating at 105° C.-110° C. for 5-10 min, and a color change to dark blue indicates a positive reaction;
5) washing: washing twice with DMF at 5-15 ml/g, twice with methanol at 5-15 ml/g, and twice with DMF at 5-15 ml/g;
6) condensation: adding 3-to-4-fold excess of a protected amino acid Fmoc-Leu-OH and 3-to-4-fold excess of HBTU, both dissolved in a small amount of DMF, into a reaction tube, followed by adding 9-to-11-fold excess of DIEA to react for 40 min;
7) washing after step 6): washing once with DMF at 5-15 ml/g, twice with methanol at 5-15 ml/g, twice with DMF at 5-15 ml/g;
8) repeating steps 2) to 7) to link amino acids in the sequence from right to left;
9) testing: washing 3-4 times with DMF at 5-15 ml/g, 2-4 times with DCM at 5-15 ml/g, twice with DMF at 5-15 ml/g, followed by draining for 10 min; and Ninhydrin test is negative;
10) washing after step 9): washing 3-4 times with methanol at 5-15 ml/g;
11) polypeptide cleavage from resin: preparing a cleavage solution according to a ratio of 1 g resin to 10 ml cleavage solution containing 94.5% TFA, 2.5% water, 2.5% EDT, and 0.5% TIS; placing the resin into a flask or a centrifuge tube based on a ratio of the resin and the cleavage solution at 5-15 ml/g under constant temperature shaking for 120 min;
12) blow drying and washing: blow drying the cleavage solution with nitrogen, and then being subjected to chromatography with ether, followed by washing with ether for six times, and then drying by volatilization at room temperature; and obtaining a crude peptide sequence;
13) oxidative cyclization: cyclizing 10 mg of the crude peptide sequence by adding 100-120 ml of 5-6% DMF solution to oxidize sulfuydryl groups.

3. The cyclic peptide according to claim 2, wherein the steps for preparation further comprises step 14): purifying the polypeptide by HPLC as below:
  1) placing 200 mg of the crude peptide into a container, dissolving with 2-5 ml of 50% acetonitrile in water, and being sonicated for 2 min;
  2) filtering the dissolved solution with a 0.45 μm filter membrane;
  3) analysis: analyzing 3 μl of the crude product by analytical HPLC; with water and acetonitrile as a mobile phase, conducting a gradient elution for 30 min, and equilibrating HPLC firstly at an initial gradient of 95% water and 5% acetonitrile to a terminal ratio of 5% water and 95% acetonitrile for 5 min, and followed by injection;
  4) preparation: making the dissolved sample ready for injection; equilibrating preparative HPLC for 10 min at an initial gradient of 95% water and 5% acetonitrile to a terminal gradient of 25% water and 75% acetonitrile for 40 min; collecting the sample from the detector.

4. A composition for repairing a bone defect, the composition comprising the cyclic peptide of claim 1.

5. The composition according to claim 4, wherein the composition further comprises a biological material, and wherein the biological material is mixed with the cyclic peptide.

6. The composition according to claim 5, wherein the biological material comprises a bioglass material, a degradable natural polymer, or a synthetic degradable polymer material.

7. The composition according to claim 6, wherein the bioglass material is selected from one or more of hydroxyapatite, dibasic calcium phosphate, tricalcium phosphate, octacalcium phosphate, and calcium sulfate.

8. The composition according to claim 6, wherein the degradable natural polymer is selected from one or more of chitosan, hyaluronate, sodium alginate, cellulose, starch, lignin, collagen, gelatin, and carrageenan.

9. The composition according to claim 6, wherein the synthetic degradable polymer material is selected from one or more of polylactic acid, polyglycolic acid, polycaprolactone, polyhydroxyalkanoate, polysiloxane, and polyurethane.

10. The composition according to claim 4, further comprising a support carrier.

11. The composition according to claim 10, wherein the carrier is selected from one of hydrogel, membrane, and sponge.

12. The composition according to claim 11, wherein the cyclic peptide has a concentration of 0.01-10 μg per cubic centimeter of carrier.

* * * * *